(12) United States Patent
Ogawa et al.

(10) Patent No.: US 8,767,200 B2
(45) Date of Patent: Jul. 1, 2014

(54) LUMINOUS FLUX BRANCHING ELEMENT AND MASK DEFECT INSPECTION APPARATUS

(71) Applicant: NuFlare Technology, Inc., Numazu (JP)

(72) Inventors: Riki Ogawa, Kanagawa (JP); Hiroyuki Nagahama, Saitama (JP); Tomohiro Nakamura, Tochigi (JP)

(73) Assignee: NuFlare Technology, Inc., Numazu-shi (JP)

( * ) Notice: Subject to any disclaimer, the term of this patent is extended or adjusted under 35 U.S.C. 154(b) by 0 days.

(21) Appl. No.: 13/737,106

(22) Filed: Jan. 9, 2013

(65) Prior Publication Data

US 2013/0176559 A1 Jul. 11, 2013

(30) Foreign Application Priority Data

Jan. 11, 2012 (JP) ................................ 2012-002882

(51) Int. Cl.
*G01N 21/00* (2006.01)
*G01N 21/95* (2006.01)
*G02B 27/10* (2006.01)

(52) U.S. Cl.
CPC ............ *G01N 21/9506* (2013.01); *G02B 27/10* (2013.01)
USPC ...................... 356/237.4; 250/201.2; 359/629

(58) Field of Classification Search
CPC ............ G01N 21/9506; G01N 21/956; G01N 2021/95676; G02B 27/10; G02B 27/108; G02B 27/144

USPC .............. 356/237.1–237.5; 250/201.2–201.4; 359/483, 484, 487, 494, 629
See application file for complete search history.

(56) References Cited

U.S. PATENT DOCUMENTS

| | | | | |
|---|---|---|---|---|
| 4,960,320 | A * | 10/1990 | Taniura | 359/285 |
| 6,369,951 | B1 | 4/2002 | Spanner | |
| 6,606,197 | B2 | 8/2003 | Amin et al. | |
| 7,791,667 | B2 * | 9/2010 | Hamano | 348/345 |
| 2005/0180297 | A1 * | 8/2005 | Takashima et al. | 369/118 |
| 2012/0038978 | A1 * | 2/2012 | Tanabe et al. | 359/372 |

FOREIGN PATENT DOCUMENTS

JP 7-311302 11/1995

* cited by examiner

*Primary Examiner* — Hoa Pham
(74) *Attorney, Agent, or Firm* — Oblon, Spivak, McClelland, Maier & Neustadt, L.L.P.

(57) ABSTRACT

A luminous flux branching element includes a transparent base member arranged diagonally to an optical axis and having an incidence plane and an emission plane parallel to each other. Incident light from the incidence plane is split into a main luminous flux emitted from an emission position on the emission plane and a branched luminous flux emitted from a branch position apart from the emission position and having a smaller light quantity than of the main luminous flux. A reflecting member is arranged on the incidence plane to cause the incidence plane to reflect reflected light from the emission plane. A non-coat region in which antireflection-treatment is not performed is formed in a region of the emission plane where the incident light from the incidence plane is reached, and antireflection-treatment is performed in the emission plane excluding the non-coat region and the incidence plane.

8 Claims, 2 Drawing Sheets

LUMINOUS FLUX BRANCHING ELEMENT AND MASK DEFECT INSPECTION APPARATUS

CROSS-REFERENCE TO RELATED APPLICATION

This application is based upon and claims the benefit of priority from prior Japanese Patent Application No. 2012-002882 filed on Jan. 11, 2012 in Japan, the entire contents of which are incorporated herein by reference.

BACKGROUND OF THE INVENTION

1. Field of the Invention

The present invention relates to a luminous flux branching element and a mask defect inspection apparatus, and in particular, relates to a luminous flux branching element arranged diagonally to incident light to split the incident light from a plane of incidence into a main luminous flux emitted from an emission position on an emission surface and a branched luminous flux emitted from a branch position apart from the emission position and having a smaller quantity of light than that of the main luminous flux and a mask defect inspection apparatus including the luminous flux branching element.

2. Related Art

A luminous flux branching element (optical element) including a luminous flux transmission portion that allows a luminous flux to be incident and a luminous flux reflection portion that reflects all or a portion of the luminous flux incident from the luminous flux transmission portion on a surface of a parallel transparent plate and provided with a luminous flux branching film having a different reflectance has been known as a luminous flux branching element.

For example, a luminous flux branching element provided with a luminous flux transmission portion that allows a luminous flux to be incident and a luminous flux reflection portion that reflects all or a portion of the luminous flux incident on a parallel plate from the luminous flux transmission portion on a surface of the parallel plate and provided with a luminous flux branching film having a different reflectance positioned in each arrival position of the luminous flux repeatedly reflected between the other surface of the parallel plate and the luminous flux reflection portion after being incident from the luminous flux transmission portion on the other surface of the parallel plate is described. (See Published Unexamined Japanese Patent Application No. 7-311302 (JP-A-7-311302), for example.)

A luminous flux branching element described below is also known as another luminous flux branching element. FIGS. 3 and 4 are schematic diagrams showing the luminous flux branching element. A luminous flux branching element 40 shown in FIG. 3 has optical branching (beam splitter, BS) coats 44, 45 whose transmittance is 70% and whose reflectance is 30% deposited on a plane of incidence 42 and a plane of emission 43 of a translucent member 41 formed of a plate made of, for example, optical glass. The luminous flux branching element 40 splits the main luminous flux quantity: branched luminous flux quantity to about 10:1.

A luminous flux branching element 50 shown in FIG. 4 has an AR coat 54 and a mirror coat 55 deposited on a plane of incidence 52 of a translucent member 51 formed of a plate made of, for example, optical glass and an AR coat 56 deposited on a plane of emission 53 in a partial range. In this case, if the incident light is S polarized light, the main luminous flux quantity:branched luminous flux quantity is split to about 10:1.

However, a general luminous flux branching element as shown in JP-A-7-311302 has gradation in the coat in order to make the quantity of light of each branched luminous flux uniform to some extent. The luminous flux branching element is suitable to split into luminous fluxes whose diameter is small, but unevenness of the quantity of light in each branched luminous flux tends to increase and thus, the luminous flux branching element is not suitable to split into luminous fluxes whose diameter is large.

The luminous flux branching element 40 shown in FIG. 3 loses 45% of the total quantity of light as reflected light, resulting in low illumination efficiency. Further, the luminous flux branching element 50 shown in FIG. 4 has unevenness of the boundary between the AR coat 54 and the mirror coat 55 of 0.1 to 1 mm, which makes it impossible to split or difficult to make adjustments when the interval between the main luminous flux and the branched luminous flux is small.

Incidentally, a mask inspection apparatus is known as an enlarging observation apparatus using such a luminous flux branching element. In the mask inspection apparatus, two branched luminous fluxes are used as a luminous flux for mask inspection and a luminous flux for autofocus. In this case, the quantity of light of the luminous flux for autofocus is small, but the luminous flux for autofocus needs to be formed in a region separate from a mask defect detection illumination region and further, a predetermined distance needs to be maintained from the region to the mask defect detection illumination region.

Thus, when the mask defect detection illumination region and the autofocus region are illuminated together, a reflected illumination region needs to be increased, which makes it impossible to use the quantity of light effectively. Therefore, the quantity of light reaching the surface of a sensor decreases, causing a problem of delayed inspection throughput.

BRIEF SUMMARY OF THE INVENTION

In accordance with one aspect of the present invention, a luminous flux branching element, includes a transparent base member arranged diagonally to an optical axis and having a plane of incidence and a plane of emission parallel to each other formed thereon, wherein incident light from the plane of incidence is split into a main luminous flux emitted from an emission position on the plane of emission and a branched luminous flux emitted from a branch position apart from the emission position and having a smaller quantity of light than that of the main luminous flux, further comprising: a reflecting member arranged on the plane of incidence to cause the plane of incidence to reflect reflected light from the plane of emission, wherein a non-coat region in which antireflection-treated is not performed is formed in a region of the plane of emission where the incident light from the plane of incidence is reached, and antireflection-treated is performed in the plane of emission excluding the non-coat region and the plane of incidence.

In accordance with another aspect of the present invention, a mask defect inspection apparatus, includes: the luminous flux branching element; a defect inspection unit that inspects for mask defects; and an autofocus unit that adjusts focus of the defect inspection unit, wherein illumination for mask defect inspection is provided based on the main luminous flux from the luminous flux branching element and the illumination for autofocus is provided based on the branched luminous flux from the luminous flux branching element.

DETAILED DESCRIPTION OF THE INVENTION

Figure 1:
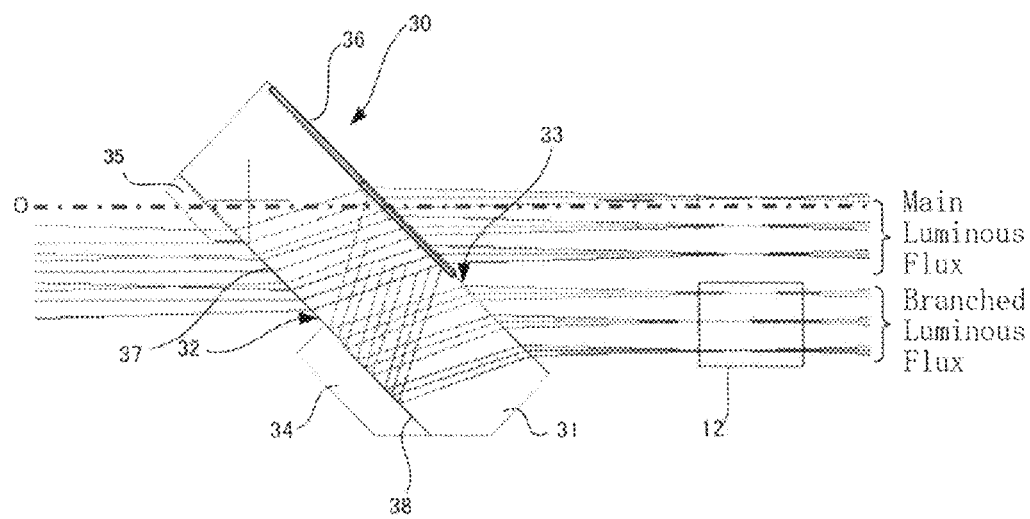
FIG. 1 is a schematic diagram showing a luminous flux branching element according to a first embodiment.

In the embodiments that follow, a luminous flux branching element capable of easily branching an incident luminous flux with less losses in the quantity of light and a mask defect inspection apparatus will be described.

First Embodiment

A luminous flux branching element in the first embodiment is a luminous flux branching element that includes a transparent base member arranged diagonally to an optical axis and having a plane of incidence and a plane of emission parallel to each other formed thereon and splits incident light from the plane of incidence into a main luminous flux emitted from an emission position on the plane of emission and a branched luminous flux emitted from a branch position apart from the emission position and having a smaller quantity of light than that of the main luminous flux. The luminous flux branching element also has a reflecting member arranged on the plane of incidence to cause the plane of incidence to reflect reflected light from the plane of emission and has a non-coat region in which antireflection-treated is not performed formed in a region of the plane of emission where the incident light from the plane of incidence is reached, and antireflection-treated is performed in the plane of emission excluding the non-coat region and the plane of incidence. Accordingly, an easily adjustable luminous flux branching element with less losses in the quantity of light can be realized with a simple configuration.

The luminous flux branching element also has a light blocking member arranged on the plane of incidence to block a portion of the plane of incidence and has an incident region where the incident light is incident formed between the light blocking member and the reflecting member. By limiting the size of luminous fluxes in this manner, the prevention of the branched luminous flux reflected in the non-coat region from being leaked to the outside of the multi-reflection mirror and the prevention of the main luminous flux and the branched luminous flux from overlapping can be implemented.

The luminous flux branching element also has a correcting unit arranged on a path of the branched luminous flux to correct an optical path length and it is suitable to set a focused position of the main luminous flux and that of the branched luminous flux to the same location. Accordingly, the focused position of the main luminous flux and that of the branched luminous flux can be set to the same location, which does not complicate the configuration of an optical apparatus containing the luminous flux branching element.

The luminous flux branching element also has an air-spacing portion provided between the base member and the reflecting member. Accordingly, the positions of the base member and the reflecting member can be adjusted precisely and easily.

The luminous flux branching element is characterized in that a portion of the incident light is reflected by Fresnel reflection in the non-coat region. Accordingly, by setting S polarized light as the incident light, a desired value as the ratio of light quantities of the main luminous flux and the branched luminous flux can be attained without special deposition treatment on the base member.

A more concrete description will be provided below. First, a luminous flux branching element according to the first embodiment will be described based on drawings.

FIG. 1 is a schematic diagram showing a luminous flux branching element according to the first embodiment. A luminous flux branching element 30 according to the first embodiment has a multi-reflection mirror 34 as a reflecting member arranged in a lower part and a light blocking member 35 arranged in an upper part across an incident region 37 formed in the center of a first surface (plane of incidence) 32 of a base member 31 as a parallel plate made of, for example, optical glass or artificial quartz. Light passes through the incident region 37 to travel toward a second surface (plane of emission) 33.

The plane of incidence 32 and the plane of emission 33 have an antireflection coat (AR coat) deposited thereon excluding a non-coat region 36 provided in an upper part of the plane of emission 33. Accordingly, a portion of incident light from the plane of incidence 32 is reflected by the non-coat region 36 while inclined 45° to an optical axis O of the incident light to travel toward the plane of incidence 32. Then, light from the non-coat region 36 is reflected by the multi-reflection mirror 34 before being emitted from the plane of emission 33.

By forming an air-spacing portion 38 between the base member 31 and the multi-reflection mirror 34 to separate the base member 31 and the multi-reflection mirror 34, it can be free to move the multi-reflection mirror 34. Therefore, arrangement adjustments of the multi-reflection mirror 34 with respect to the base member 31 are made easier so that the precision of interface can be improved to about 0.1 mm. The air-spacing portion 38 is provided between the base member 31 and the multi-reflection mirror 34 as described above to be able to make position adjustments of reflected light and therefore, the multi-reflection mirror 34 can be used as a 45° reflecting mirror including reflectance properties like those of a conventional reflecting mirror.

Most of light having passed through an incident region portion between the light blocking member 35 and the multi-reflection mirror 34 of the plane of incidence 32 passes through the base member 31 to become the main luminous flux.

A portion of light reflected by the plane of emission 33 of the base member 31, on the other hand, is reflected by the multi-reflection mirror 34 and emitted from the plane of emission 33 to become a branched luminous flux. In the luminous flux branching element 30 according to the embodiment, an optical path length of the main luminous flux and that of a branched luminous flux are made equal by arranging an optical path length correcting plate 12 on the optical path of the branched luminous flux.

Generally in a mask inspection apparatus using the luminous flux branching element 30, the main luminous flux and the branched luminous flux of the luminous flux branching element 30 need to be split in the ratio of about 10:1, which requires ingenuity for deposition. Thus, by changing incident light to S polarized light before entering the base member 31 to cause Fresnel reflection by the non-coat region of the base member 31, the ratio of intensity of the main luminous flux and the branched luminous flux can be made about 10:1 so that the process of deposition onto the base member 31 can be reduced. The reflectance Rs of S polarized light is represented by Formula (1) shown below:

$$R_s = \left(\frac{n_1\cos\theta_1 - n_2\cos\theta_2}{n_1\cos\theta_1 + n_2\cos\theta_2}\right)^2 \quad (1)$$

$n_1$ indicates refractive index of incident side and $n_2$ indicates refractive index of transmission side. $\theta_1$ indicates an angle of incident light and $\theta_2$ indicates an angle of transmission light. The center wavelength $\lambda$, is set to 198.5 nm and the index of refraction of artificial quartz n is set to 1.5526. From the above formula, the reflectance of S polarized light of the non-coat region 36 of the multi-reflection plate becomes 10.44% and if absorption by the AR film, the multi-reflection mirror 34, and the base member 31 after reflection by the non-coat region 36 is taken into consideration, the calculated value of the ratio of light quantities is approximately as follows: main luminous flux intensity:branched luminous flux intensity=10:1.

According to a luminous flux branching element according to the first embodiment, as described above, an easily adjustable luminous flux branching element with less losses in the quantity of light can be realized with a simple configuration.

Second Embodiment

A mask defect inspection apparatus according to the second embodiment includes the luminous flux branching element, a defect inspection unit that inspects for mask defects, and an autofocus unit that adjusts the focus of the defect inspection apparatus. Then, the illumination for mask defect inspection is provided based on the main luminous flux from the luminous flux branching element and the illumination for autofocus is provided based on the branched luminous flux from the luminous flux branching element.

Because the luminous flux branching element is thereby used in a mask defect inspection apparatus, the ratio of light quantities and the spaced distance between the main luminous flux and the branched luminous flux can be made appropriate and losses of light from a light source can be prevented without complicating the configuration of an optical system. A more concrete description will be provided below.

Figure 2:
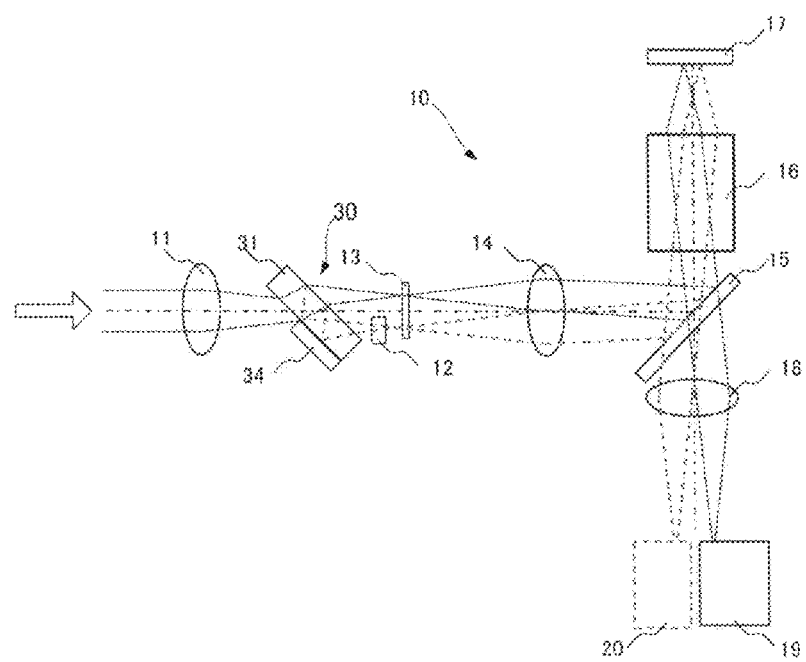
FIG. 2 is a schematic diagram showing an optical system of a mask defect inspection apparatus according to a second embodiment.
Figure 3:
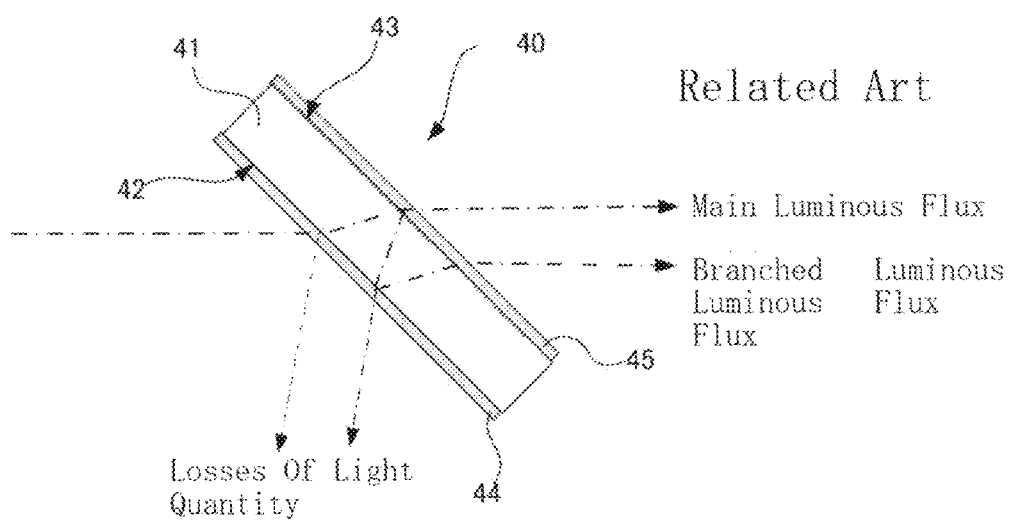
FIG. 3 is a schematic diagram showing the luminous flux branching element.
Figure 4:
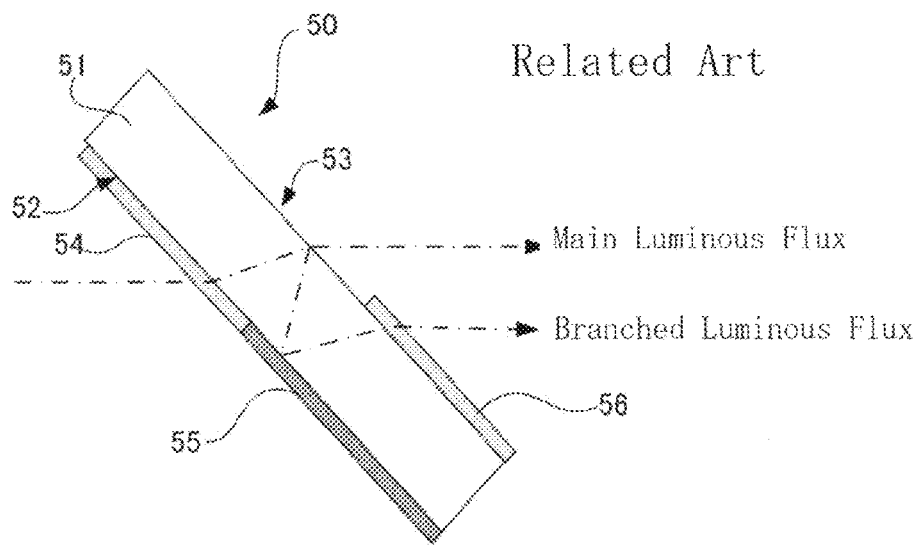
FIG. 4 is a schematic diagram showing the luminous flux branching element.

Next, a mask defect inspection apparatus 10 as an enlarging observation apparatus using the luminous flux branching element 30 will be described. FIG. 2 is a schematic diagram showing an optical system of a mask defect inspection apparatus according to the second embodiment.

The mask defect inspection apparatus 10 inspects a mask 17 as an inspection target. The mask defect inspection apparatus 10 includes a light source (not shown), a collimator lens 11, the luminous flux branching element 30, the optical path length correcting plate 12, a diaphragm 13, a tube lens 14, a beam splitter 15, an objective lens 16, an image-forming lens 18, a mask defect detection sensor 19, and an autofocus sensor 20.

In the mask defect inspection apparatus 10, the luminous flux from the same light source is branched by the luminous flux branching element 30 to illuminate the mask defect detection sensor 19 to detect defects of the mask 17 and the autofocus sensor 20 used to fine-tune the height of the mask 17.

The luminous flux such as laser light emitted from the light source illuminates the position of the diaphragm 13 by means of the collimator lens 11. At this point, the luminous flux is split into the main luminous flux and the branched luminous flux by the luminous flux branching element 30 between the collimator lens 11 and the diaphragm 13. The luminous flux branching element 30 spatially separates an incident luminous flux into the main luminous flux and the branched luminous flux a predetermined distance apart and also splits the incident luminous flux in a desired ratio of light quantities (for example, main luminous flux:branched luminous flux=10:1). Thus, the illumination efficiency can be enhanced.

The main luminous flux is used for mask defect inspection and the branched luminous flux is used for autofocus. The quantity of light of the luminous flux needed by the autofocus sensor 20 may be small, but the luminous flux needs to be formed in a separate range from the illumination for mask defect detection for detection by the mask defect detection sensor 19 and also needs to be a predetermined distance apart from the illumination.

Further, the main luminous flux and the branched luminous flux are reflected by the beam splitter 15 after passing through the tube lens 14 and a reflected luminous flux illuminates a pattern formation surface of the mask 17 via the objective lens 16.

Because the pattern formation surface (inspection target surface) of the mask 17 is a conjugate position with respect to the diaphragm 13, respective illumination regions by the main luminous flux and the branched luminous flux adjusted by the diaphragm 13 are formed on the pattern formation surface.

Then, after both luminous fluxes being reflected by the mask 17, the reflected light of the main luminous flux forms an image on the mask defect detection sensor 19 and the reflected light of the branched luminous flux forms an image on the autofocus sensor 20 via the objective lens 16 and the image-forming lens 18.

According to the mask defect inspection apparatus 10 in the second embodiment, as described above, a luminous flux is split into the luminous flux for mask defect detection and the luminous flux for autofocus by the luminous flux branching element 30 and therefore, the ratio of light quantities and the spaced distance between both luminous fluxes can be made appropriate and losses of light from a light source can be prevented without complicating the configuration of an optical system.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A luminous flux branching element, comprising
a transparent base member, arranged diagonally to an optical axis, having a plane of incidence and a plane of emission parallel to each other,
wherein incident light from the plane of incidence is split into a main luminous flux emitted from an emission position on the plane of emission and a branched luminous flux emitted from a branch position apart from the emission position of which has quantity smaller than that of the main luminous flux, further comprising:
a reflecting member arranged on the plane of incidence to cause the plane of incidence to reflect reflected light from the plane of emission,
wherein a non-coat region in which antireflection-treated is not performed is formed in a region of the plane of emission where the incident light from the plane of incidence is reached, and
antireflection-treated is performed in the plane of emission excluding the non-coat region and the plane of incidence.

2. The element according to claim 1, further comprising a light blocking member arranged on a portion of the plane of incidence,
wherein an incident region where the incident light is incident is formed between the light blocking member and the reflecting member.

3. The element according to claim 1, further comprising a correcting unit arranged on a path of the branched luminous flux to correct an optical path length,
wherein a focused position of the main luminous flux and that of the branched luminous flux are set to a same location.

4. The element according to claim 1, wherein an air-spacing portion is formed between the base member and the reflecting member.

5. The element according to claim 1, wherein a portion of the incident light is reflected in the non-coat region by Fresnel reflection.

6. The element according to claim 1, wherein the incident light is changed to S polarized light before entering the transparent base member.

7. A mask defect inspection apparatus, comprising:
a luminous flux branching element having a transparent base member, arranged diagonally to an optical axis, having a plane of incidence and a plane of emission parallel to each other to split incident light from the plane of incidence into a main luminous flux emitted from an emission position on the plane of emission and a branched luminous flux emitted from a branch position apart from the emission position of which has quantity smaller than that of the main luminous flux, wherein a reflecting member is arranged on the plane of incidence to cause the plane of incidence to reflect reflected light from the plane of emission, a non-coat region in which antireflection-treated is not performed is formed in a region of the plane of emission where the incident light from the plane of incidence is reached, and antireflection-treated is performed in the plane of emission excluding the non-coat region and the plane of incidence;
a defect inspection unit that inspects for mask defects; and
an autofocus unit that adjusts focus of the defect inspection unit,
wherein illumination for mask defect inspection is provided based on the main luminous flux from the luminous flux branching element and the illumination for autofocus is provided based on the branched luminous flux from the luminous flux branching element.

8. The apparatus according to claim 7, wherein the incident light is changed to S polarized light before entering the transparent base member.

* * * * *